United States Patent [19]

Brown et al.

[11] Patent Number: 4,701,159
[45] Date of Patent: Oct. 20, 1987

[54] MULTILUMEN CATHETER SET

[75] Inventors: Eric W. Brown, Redondo Beach; Henry T. Tai, Pacific Palisades, both of Calif.

[73] Assignee: I-Flow Corporation, Irvine, Calif.

[21] Appl. No.: 795,906

[22] Filed: Nov. 7, 1985

Related U.S. Application Data

[63] Continuation-in-part of Ser. No. 678,481, Dec. 5, 1984, Pat. No. 4,581,012.

[51] Int. Cl.$^4$ ............................................. A61M 25/00
[52] U.S. Cl. ...................................... 604/43; 604/175; 604/256; 604/283; 285/137.1
[58] Field of Search .................................. 604/43–45, 604/51–53, 173, 241–242, 175, 905, 283, 256, 103; 285/137.1

[56] References Cited

U.S. PATENT DOCUMENTS

| 2,674,265 | 4/1954 | Dennis | 604/173 X |
| 3,747,632 | 6/1973 | Kok et al. | 285/137.1 |
| 3,805,794 | 4/1974 | Schlesinger | 604/103 |
| 4,133,312 | 1/1979 | Burd | 604/175 X |
| 4,187,846 | 2/1980 | Lolachi et al. | 604/905 X |
| 4,327,722 | 5/1982 | Groshong et al. | 604/169 X |
| 4,340,148 | 7/1982 | Beckham | 604/241 X |
| 4,367,740 | 1/1983 | Evanoski | 604/43 |
| 4,405,313 | 9/1983 | Sisley et al. | 604/43 |
| 4,551,130 | 11/1985 | Herbert et al. | 604/256 X |
| 4,578,063 | 3/1986 | Inman et al. | 604/175 |
| 4,581,012 | 4/1986 | Brown et al. | 604/43 |
| 4,585,435 | 4/1986 | Vaillancourt | 604/44 X |
| 4,600,015 | 7/1986 | Evans et al. | 604/100 X |
| 4,601,701 | 7/1986 | Mueller | 604/256 X |

FOREIGN PATENT DOCUMENTS

| 0033080 | 3/1983 | European Pat. Off. . |
| 2845346 | 4/1980 | Fed. Rep. of Germany | 604/283 |
| 3005964 | 8/1981 | Fed. Rep. of Germany . |
| WO83/00812 | 8/1983 | PCT Int'l Appl. . |

Primary Examiner—Dalton L. Truluck
Attorney, Agent, or Firm—Robert M. Asher

[57] ABSTRACT

A subcutaneous catheter set is disclosed in which a multilumen catheter tube has a tissue cuff connected about its outer circumference. A lock adapter has a plurality of conduits in communication with the lumens of the multilumen catheter tube. A complementary lock adapter is connected to either another multilumen catheter tube, a plurality of single lumen lines, a plurality of injection tubes or may be plugged to act as a seal. The two lock adapters can be locked together so that the subcutaneous multilumen catheter may be connected directly to any of the items attached on the complementary lock adapter.

17 Claims, 14 Drawing Figures

MULTILUMEN CATHETER SET

This is a continuation-in-part of U.S. Ser. No. 678,481 filed Dec. 5, 1984, now U.S. Pat. No. 4,581,012 issued Apr. 8, 1986.

BACKGROUND OF THE INVENTION

This invention relates to a multilumen catneter set, in particular, one for a subcutaneous route for intravenous infusions.

It has been found convenient for patients who are receiving frequent infusions to provide them with a tunneled subcutaneous catheter. Such a catheter is inserted underneath the skin of the patient and then into a vein. A tissue cuff is provided on the catheter near the skin so that the skin may grow into it and hold the catheter in place. An adapter is located on the end of the catheter, above the skin. Into which a mating connector may be attached to connect the subcutaneously tunneled catheter with an external catheter. The external catheter may be used for infusion of fluids or for extraction of body fluid for testing.

Since there are times when more than one infusion or operation using the catheter set may be desirable, dual lumen subcutaneously tunneled catheters have been developed. The two lumens are fused together underneath the skin of the patient. Above the skin the lumens are separated and each is provided with an adapter for separate connection to an outside source. This arrangement can be cumbersome for a patient since there are two tubes and adapters hanging from the implanted catheter and would be even more cumbersome if the implanted catheter has more than two lumens. Furthermore, if one of the single lumen extensions projecting from the implanted multilumen catheter should break off, the entire catheter set may need to be surgically replaced.

Experimentation and advances in medicine are creating new needs for infusing a multiplicity of fluids into a patient. There are many applications for which there is a need for a device which can intravenously administer a plurality of drug solutions. One such application is the use of chemotherapy to treat such diseases as cancer. Attempts at providing more advanced chemotherapy regimens involving the intravenous administration of a multiplicity of drug solutions are being inhibited by a lack of equipment to simplify such a procedure. Very often, if different drug solutions are used, they are administered by using a separate catheter tube for each drug. This may require a separate pump for each catheter tube line which would increase costs.

There is thus a need for new catheter equipment which offers greater patient comfort and provides doctors with greater convenience in experimenting and using new treatments that involve a plurality of drug solutions.

SUMMARY OF THE INVENTION

The present invention is directed to a subcutaneously tunneled catheter set which includes a multilumen catheter for insertion under the skin of a patient. The catheter includes a tissue cuff about its outer circumference. At the outermost end of the catheter, a lock adapter of the present invention is attached. The adapter includes a plurality of ports for connection with each of the lumens in the catheter. A conduit is located in the adapter between each port and a mating face. A complementary lock adapter is attached to an external multilumen catheter, a plurality of single lumen access lines, or a plurality of injection tubes. The complementary lock adapter may instead have solid protrusions for closing off conduits of said first adapter or may have a combination of single lumen catneters, injection tubes and solid protrusions. A device is provided for locking the two adapters together. They are locked in such a way that the conduits provide communication between the lumens of the subcutaneously tunneled catheter and the lumens of the external multilumen catheter, the single lumen access lines, the injection tubes, or the solid protrusions depending upon which are carried by the complementary lock adapter.

The subcutaneously tunneled catheter may be connected by a multilumen connector to a second reinforced multilumen catheter. The multilumen connector may advantageously be tube. The multilumen connector may advantageously be provided with a tissue cuff about its circumference so that one will not be required about the catheter.

The multilumen catheter set of the present invention advantageously provides the ability for long term regimens of drug treatment involving a plurality of drug solutions. The wire reinforced catheter may be used to advantageously avoid blockage of the catheter because of bending of the catheter tube. The multilumen locking connector advantageously allows the use of a variety of different external input devices with the subcutaneously tunneled catheter set.

A single pump which may be used in conjunction with the catheter set of the present invention is described in pending patent application U.S. Ser. No. 677,849, filed Dec 5, 1984 entitled "Infusion Pump", sharing the same assignee as the present invention. The disclosure of said application is hereby incorporated by reference herein.

Other objects and advantages of the present invention will become apparent during the following description of the presently preferred embodiment of the invention taken in conjunction with the drawings.

DETAILED DESCRIPTION OF THE PREFERRED EMBODIMENT

Figure 1:
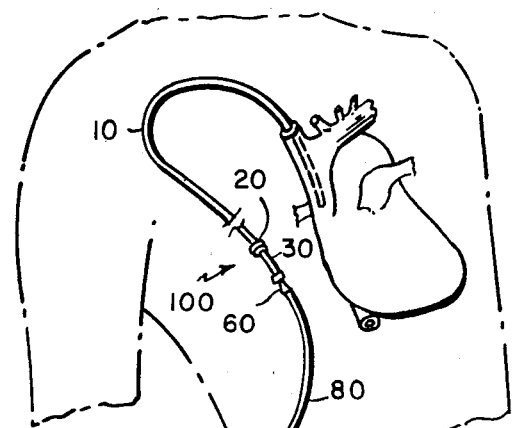
FIG. 1 is an illustration of the catheter set of the present invention being used in a patient.

Referring now to FIG. 1, the multilumen subcutaneously tunneled cather set 100 of the present invention is inserted and used in a patient in a manner similar to that of the well known Hickman catheter sets. According to the present invention. A subcutaneously tunneled multilumen catheter tube 10 is surgically inserted under the skin and into a vein of the patient. The lumens are provided with an exit port 12 at the end of the multilumen catheter tube 10. Near the other end of the subcutaneously tunneled multilumen catheter tube there is a tissue cuff 20 into which fibrous tissue of the patient grows to anchor the catheter set and to reduce the likelihood of infection.

Figure 2:
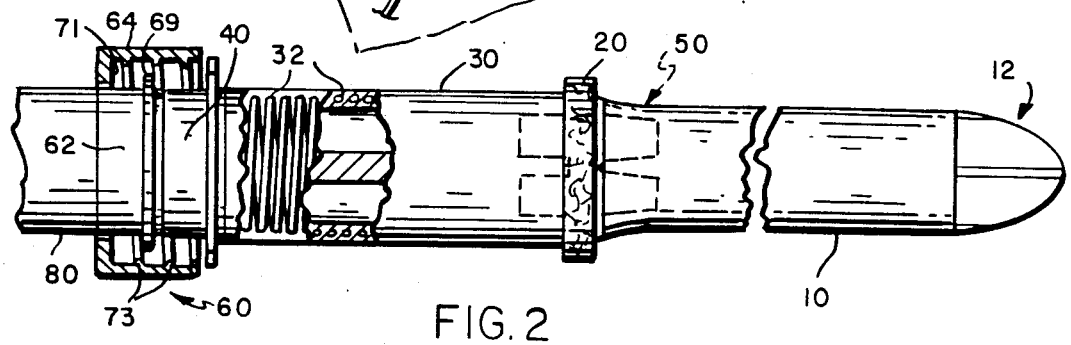
FIG. 2 is a plan view of a first embodiment of the catheter set of the present invention in partial cross-section.
Figure 8:
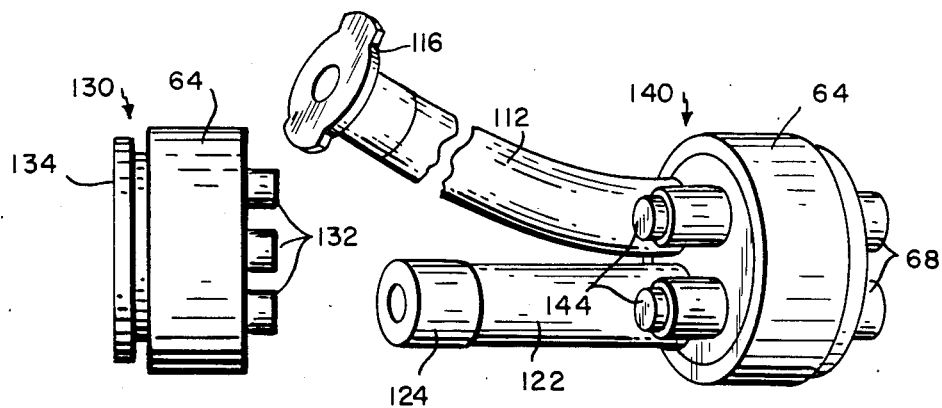
FIG. 8 is a plan view of the sealing cap of the present invention.

A reinforced catheter tube 30 extends from the tissue cuff 20 out of the patient and ends with a multilumen locking connector adapter 40. Since the catheter tubes are very small in diameter, bending a multilumen catheter tube may have a tendency to close off one of the lumens with a kink in the outer layer of tubing. To make the exterior catheter tube kink-proof, reinforcement is provided in the multilumen catheter 30. In accordance with the preferred reinforcement as shown in FIG. 2, the catheter 30 is reinforced with a wire coil 32. The wire coil 32 may be additionally used in some applications to conduct electrical information from a sensor located at the patient's body back to diagnostic instruments. The multilumen locking connector adapter 40 is covered with a sealing cap such as that shown in FIG. 8 when the catheter set is not in use. In a multilumen catheter, since the walls of each lumen are often much smaller than the walls of a single catheter tube, the likelihood of a blockage due to kinking when the tube is bent is greater. To make the exterior catheter tube kink-proof, reinforcement is provided in the multilmen catheter 30. In accordance with the preferred embodiment as shown in FIG. 2, the catheter 30 is reinforced with a wire coil 32. The wire coil 32 may be additionally used in some applications to conduct electrical information from a sensor located at the patient's body back to diagnostic instruments.

Figure 3:
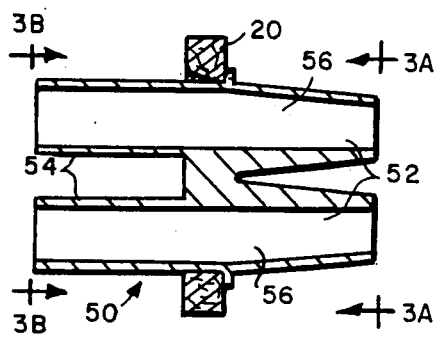
FIG. 3 is a cross-sectional view of the multilumen connector of the present invention.
Figure 3A:
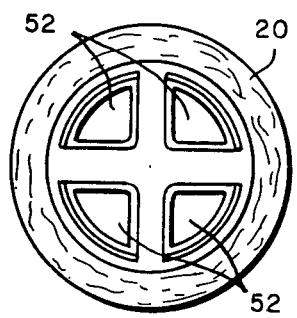
FIG. 3A is an end view of the multilumen connector of FIG. 3 taken along lines A—A.
Figure 3B:
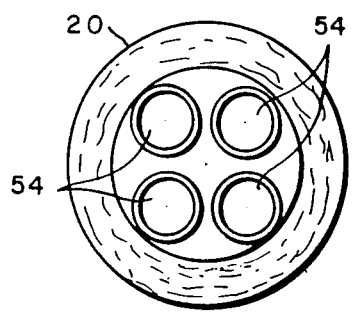
FIG. 3B is an end view of the multilumen connector of FIG. 3 taken along lines B—B.

Referring now to FIGS. 3, 3A and 3B, the multilumen connector of the present invention is shown. This connector 50 has a plurality of ports 52 at one end onto which the lumens of the suocutaneously tunneled multilumen catheter tube 10 are bonded in a conventional manner. At the opposite end of the connector 50, a corresponding plurality of ports 54 are provided for bonding with the lumens of the reinforced catheter 30. The shaoes of the lumens illustrated in FIGS. 3A and 3B differ. Nevertheless, the lumens in the multilumen catheters of the present invention may be any useable shape and they may be the same at both ends of the connector 50. It is desirable, however, that the lumens be shaped in the subsutaneously tunneled multilumen catheter tube so that the maximum amount of fluid flow is allowed in a minimum amount of space. The ports 52 and 54 at opposite ends of the connectors are in communication with one another via conduits 56. Thus, when the connector is hooked up on either end to multilumen catheter tube, the lumens of the two tubes are in communication with one another. According to the present invention, the preferred placement for the tissue cuff 20 is around the outer circumference of the multilumen connector 50 as shown in FIG. 3. The cuff 20 may be glued, thermally melted or bonded to the connector 50 by any other conventional bonding method.

Figure 4B:
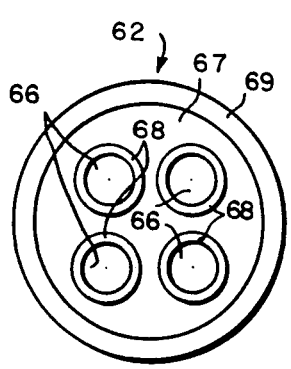
FIG. 4B is an end view of the multilumen locking connector of FIG. 4 taken through lines B—B.
Figure 4:
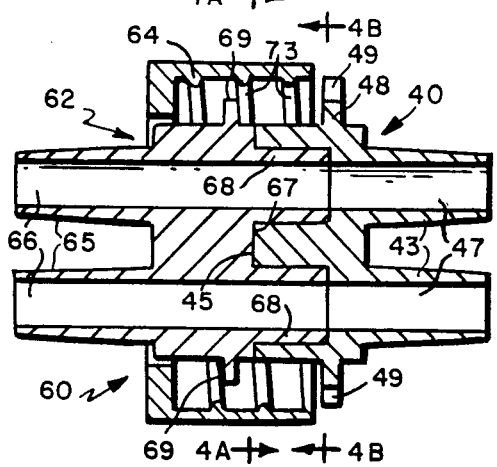
FIG. 4 is a cross-sectional view of the multilumen locking connector of the present invention.
Figure 4A:
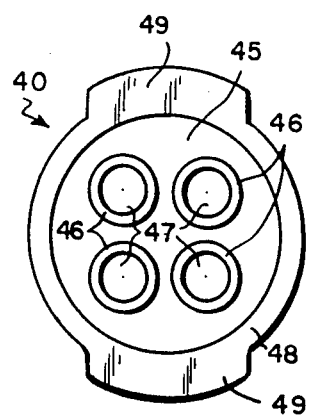
FIG. 4A is an end view of the multilumen locking connector of FIG. 4 taken through lines A—A.

FIGS. 4, 4A and 4B illustrate the multilumen locking connector for connecting the catheter set of the present invention with an external multilumen catheter tube 80. The external multilumen catheter tube 80 is preferably reinforced to avoid kinking. According to the preferred embodiment the multilumen locking connector 60 is made with a female lock adapter 40, a male lock adapter 62 and a locking ring 64. The female lock adapter 40 includes a plurality of ports 43 onto which the lumens of the reinforced catheter tube 30 are bonded. On the opposite side of the female lock adapter 40 is a mating face 45 which includes a plurality of incentations 46. A conduit 41 passes from each port 43 to the mating face 45. The indentations 46 are located at each conduit 42. A ring 48 including two tabs 49 is shown surrounding the outer circumference of the female adapter 40. The tabs 49 are used for engaging the locking ring 64.

The male multilumen lock adapter 62 is likewise provided with a plurality of ports 65 for fitting within and bonding to its respective multilumen catheter tube. Conduits 66 connect each port 65 to the mating face 67 at the other end of the male adapter 62. The mating face 67 of the male lock connector includes a protrusion 68 at each conduit 66. The protrusions 68 match the indentations 46 of the female lock connector 40 so that the two mating faces 67 and 45 may be interengaged.

The lumens in a multilumen catheter are symmetrically arranged about the center. The conduits in the multilumen locking connector 60 may likewise be symmetrically arranged. However, it may be useful to provide asymmetry or a matching groove and notch in the two mating faces so that the mating faces cannot be interengaged in any other than one position. This will ensure that each time an exterior multilumen catheter tube 80 is attached to the subcutaneously tunneled multilumen catherter set 100 the same lumens will be connected. Therefore, the same drug solutions may be delivered through the plurality of lumens without fear of unwanted mixing in the subcutaneously tunneled catheter set 100. The asymmetry about the center may be provided by giving an irregular shape to one or more of the protrusions and indentations or by an asymmetric positioning of the protrusions and indentations which may be accommodated by directing the conduits in other than a straight line.

The male lock adapter 62 is provided with a shoulder 69 on its outer circumference. The shoulder 69 is provided for abutment against the locking ring 64. The locking ring 64 includes a base 71 and a set of inner threads 73. The base 71 encircles the male lock adapter 62 and is located at the side of the shoulder 69 near the ports 65. Upon interengagement of the faces of the male and female lock adapters. the locking ring 64 may be screwed onto the female lock adapter 40. The tabs 49 of the female lock adapter 40 engage the threads 73 of the locking ring 64 as it is being screwed. When the base 71 of the ring 64 comes into abutment with the shoulder 69 of the male lock adapter 62, the locking ring 64 will be pulling the male and female lock adapters together and may thereby provide a tight seal.

Figure 5:
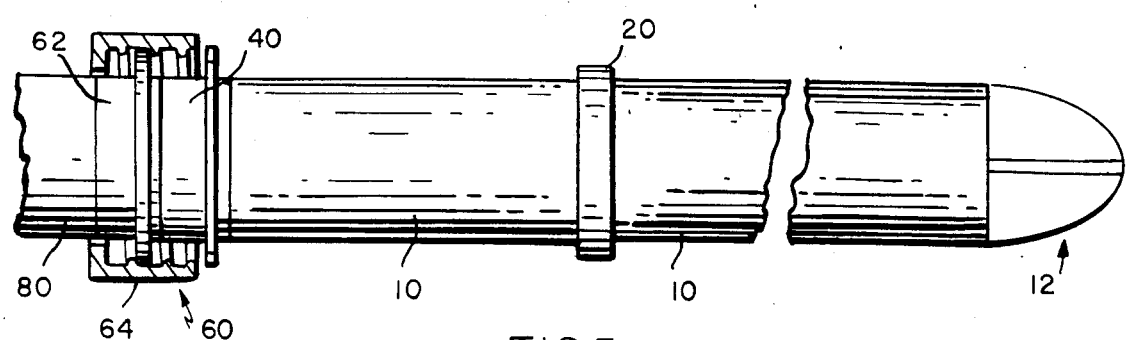
FIG. 5 is a plan view of a second embodiment of the present invention.

According to a second embodiment of the present invention, it may be uneconomical at times to provide a wire reinforced catheter. As shown in FIG. 5, a single multilumen catheter 10 may be provided with a tissue cuff 20 near its external end. The length of the catheter extending from the patient may be minimized to help avoid kinking. A female lock adapter 40 is connected to the end of the multilumen catheter 10 to provide easy attachment of a variety of adapters, caps and catheters to the implanted catheter. In FIG. 5, the lock adapter 40 is connected to a male lock adapter 62 which is attached to an external multilumen catheter 80.

Figure 6:
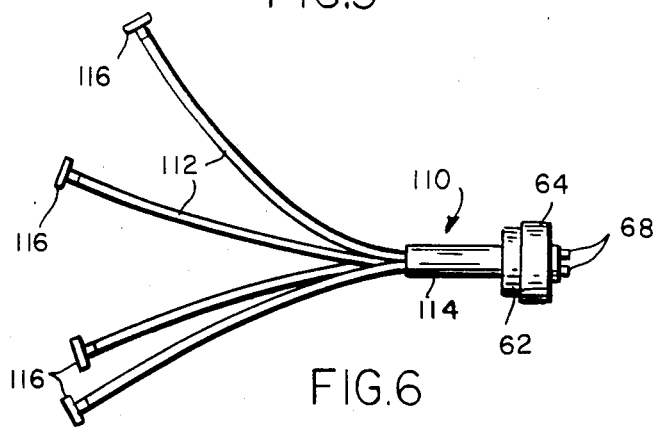
FIG. 6 is a plan view of a multibranch adapter of the present invention.

Referring now to FIG. 6, a multibranch adapter 110 is shown which may be locked onto a multilumen catheter set. The adapter includes a male lock adapter 62 for making a locking connection to the female lock adapter 40 of the subcutaneously tunneled catheter. A single lumen access line 112 is bonded by conventional methods to each of the ports 65 of the male lock adapter. The single lumen access lines 112 may be provided with luer fittings 116 at their outer ends. The luer fittings allow the lumens to be connected in a conventional manner to syringes, pumps, monitors or other hospital equipment having complementary luer fittings. In the preferred embodiment, a protective sheath 114 is located around the bundle of single lumen lines adjacent the rear of the male lock adapter. The protective sheath 114 helps to strengthen the multibranch adapter 110 to help prevent a single lumen line from breaking off from the adapter. However, if a single access line should break off, it is only necessary with the present invention to replace the multibranch adapter with a new multibranch adapter. This is an advantage over prior art catneter sets in which a broken access line may require surgical replacement of the catheter set.

Figure 7A:
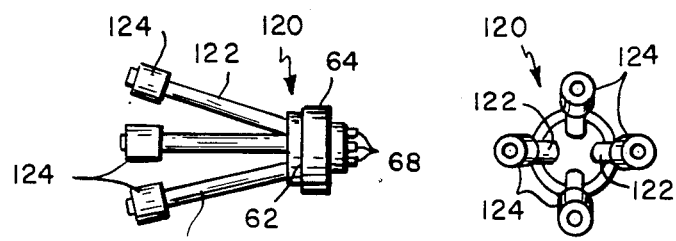
FIG. 7A is a plan view of the lock adapter of the present invention fitted with injection tubes.
Figure 7B:
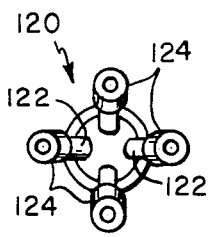
FIG. 7B is a bottom view of the lock adapter of FIG. 7A.

Rather than proceeding with a long infusion process, there are occasions on which a doctor wishes to inject drugs from a syringe into an implanted catheter set or withdraw blood from an implanted catherer set using a syringe. An injection adapter 120 as shown in FIGS. 7A and 7B, provides the doctor with the ability to use a syringe with a standard hypodermic needle to inject fluids into a patient. The injection adapter includes a male lock adapter 62 and a plurality of injection tubes 122 bonded the ports 65 of the male lock adapter 62. The injection tubes 122 are made of rapid plastic tubing which is difficult to pierce. Termination plugs 124 fit into the ends of the injection tubes 122. The plugs 124 are made of a self-sealing rubber, such as silicone. A needle may be inserted through a plug 124 to withdraw blood or inject a fluid. Upon withdrawing the needle from the plug 124, the plug reseals itself.

When the multilumen catheter set is not in use. It is desirable to place a sealing cap 130 on the female adapter 40. The sealing cab 130 is constructed like a male lock adapter 62, however, rather than conduits 66, the sealing cab 130 has solid protrusions 132. Alternatively, a male lock adapter 62 may be used in conjunction with plugs which fit into the conduits 66 to block any fluid flow through the conduits. The sealing cap 130 includes a top shoulder 134 which keeps locking ring 64 from coming off the cab.

Figure 9:
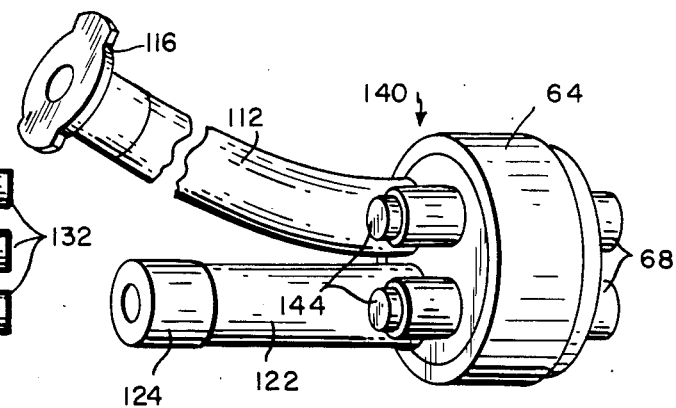
FIG. 9 is a perspective view of a multipurpose adapter of the present invention.

A multipurpose cap which combines the functions of the injection adapter, octopus adapter and sealing cab is also possible. Referring to FIG. 9, the mutipurpose cap 140 includes an injection tube 122, a single lumen access line 112 and two plugs 144. Although only one particular combination is illustrated, any other desirable combination of injection tubes, single lumen access lines and plugs is also possible. The multipurpose cap shown in FIG. 9 permits infusion of a fluid through one lumen of the catheter set and hypooermic injections through a second lumen of the set.

According to the present invention, it is no longer necessary to provide a number of single lumen catheters for infusing a patient with a plurality of drug solutions. Single lumens may be used, if desired, but the present invention advantageously provides the ability to hook a single multilumen catheter to the patient for provision of an infusion regimen involving a number of drug solutions. Therefore, only a single pump is required to provide an infusion of fluids to the patient. Using a multilumen catheter is especially advantageous where the drug solutions may not be mixed together and provided in a single tube. A further advantage of the present invention is that only a single sealing cap is required to close off the implanted catheter set. Prior art multilumen systems which have a number of single lumen catheters hanging from the patient would require a cap for each lumen. These prior art catheter sets are more bulky, are more susceptible to being pulled upon while a patient is dressing or undressing and are more noticeable under clothing.

Of course, it should be understood that various changes and modifications to the preferred embodiment described above will be apparent to those skilled in the art. For example, a snapping mechanism may be used to replace the screwable locking ring of the multilumen locking connector. Also, any appropriate number of lumens may be used, the invention is not restricted to the four shown. These and other changes can be made without departing from the spirit and scope of the invention and without diminishing its attendant advantages. It is therefore intended that such changes and modifications be covered by the following claims.

We claim:
1. A multilumen catheter set comprising:
 a first lock adapter including a plurality of conduits providing communication between a plurality of openings in a front face of said first lock adapter and a plurality of ports in a rear face of said first lock adapter;
 a multilumen catheter;
 a second lock adapter having a plurality of conduits in communication with the lumens of said multilumen catheter;
 means for locking said first lock adapter to said second lock adapter, said locking means being operable to put the conduits of said second lock adapter in communication through the front face of said first lock adapter with the conduits of said first lock adapter; and
 at least one independent single lumen access line each having one end connecting to one of said ports.

2. The multilumen catheter set of claim 1 further comprising a sheath surrounding all of said at least one independent single lumen access lines adjacent the rear face of said first lock adapter.

3. The multilumen catheter set of claim 1 further comprising a luer fitting connected to a second end of each of said at least one independent single lumen access lines.

4. The multilumen catheter set of claim 1 wherein said locking means comprise shoulder means extending from first lock adapter and an internally threaded lock ring having a base abutting said shoulder means so that when said ring is screwed onto the second lock adapter, said first lock adapter is brought into sealing contact with said second lock adapter.

5. The multilumen catheter set of claim 1 further comprising protrusions extending from the front face of said first lock adapter, each protrusion having one of said conduits therethrough.

6. An injection adapter for a multilumen catheter set comprising:
   a first lock adapter including a plurality of conduits providing communication between a plurality of openings in a front face of said first lock adapter and a plurality of ports in a rear face of said first lock adapter;
   a lock ring for achieving locking engagement between said first lock adapter and a second lock adapter having a plurality of conduits so that the conduits of said second lock adapter are in communication through the front face of said first lock adapter with the conduits of said first lock adapter; and
   at least one rigid injection tube each having one end connected to one of said ports and an other end covered with a plug penetrable by a needle and resealable so that when a needle inserted through said plug into said tube is withdrawn said plug reseals said other end of said injection tube.

7. The injection adapter of claim 6 further comprising a single lumen access line connected to one of the ports on said first lock adapter.

8. The injection adapter of claim 6 further comprising shoulder means extending from said first lock adapter and wherein said lock ring is internally threaded and has a base abutting said shoulder means so that when said ring is screwed onto the second lock adapter, said first lock adapter is brought into sealing contact with said second lock adapter.

9. The injection adapter of claim 6 further comprising protrusions extending from the front face of said first lock adapter, each protrusion having one of said conduits therethrough.

10. A sealing cap for a multilumen catheter set comprising:
    a first lock adapter including a plurality of protrusions in a front face, at least one of said protrusions being solid; and
    a lock ring for achieving locking engagement between said first lock adapter and a second lock adapter having a plurality of conduits in communication with the lumens of a multilumen catheter, said first lock adapter engaging said second lock adapter so that when locked each of said at least one solid protrusions matingly engages one of said conduits to close off said one of said conduits.

11. The sealing cap of claim 10 further comprising shoulder means extending from said first lock adapter and wherein said lock ring is internally threaded and has a base abutting said shoulder means so that when said ring is screwed onto the second lock adapter, said first lock adapter is brought into sealing contact with said second lock adapter.

12. The sealing cap of claim 10 wherein said at least one solid protrusion comprises a plurality of protrusions such that upon locking said first lock adapter to said second lock adapter, each of said conduits is closed off by one of said protrusions.

13. The sealing cap of claim 10 wherein one of said protrusions has a conduit therethrough and further comprising
    a rigid injection tube having one end connected to the conduit and an other end covered by a plug penetrable by a needle and resealable so that when a needle inserted through said plug into said tube is withdrawn said plug reseals said other end of said injection tube.

14. The sealing cap of claim 10 wherein one of said protrusions has a conduit therethrough and further comprising
    a single lumen access line connected to the conduit.

15. A subsutaneous catheter set comprising:
    a multilumen catheter tube having one end with an exit port for each lumen and an other end;
    a tissue cuff connected around an outer circumference of said catheter tube;
    a lock adapter including a plurality of ports connected to the lumens of said catheter tube and a plurality of conduits each connected to one of said ports;
    a sealing cap having a plurality of solid protrusions interengageable with said plurality of conduits of said lock adapter; and
    means for locking said lock adapter to said sealing cap so that said protrusions sealingly close each of said conduits of said lock adapter.

16. A subcutaneous catheter set comprising:
    a multilumen catheter tube having one end with an exit port for each lumen and an other end;
    a tissue cuff connected around an outer circumference of said catheter tube;
    a first lock adapter including a plurality of ports connected to the lumens of said catheter tube and a plurality of conduits each connected to one of said ports;
    a second lock adapter having a plurality of protrusions interengageable with said plurality of conduits of said first lock adapter, at least one of said protrusions having a conduit therethrough;
    at least one rigid injection tube, each having one end connected to the conduit in one of said at least one of said protrusions and an other end covered by a plug penetrable by a needle and resealable so that when a needle inserted through said plug into said tube is withdrawn, said plug reseals said other end of said at least one injection tube; and
    means for locking said first lock adapter to said second lock adapter so that said protrusions are sealingly engaged with said conduits of said first lock adapter.

17. A subcutaneous catheter set comprising:
    a multilumen catheter tube having one end with an exit port for each lumen and an other end;
    a tissue cuff connected around an outer circumference of said catheter tube;
    a first lock adapter including a plurality of ports connected to the lumens of said catheter tube and a plurality of conduits each connected to one of said ports;
    a second lock adapter having a plurality of protrusions interengageable with said plurality of conduits of said first lock adapter, at least one of said protrusions having a conduit therethrough;
    at least one single lumen access line, each connected to said conduit in one of said at least one of said protrusions; and
    means for locking said first lock adapter to said second lock adapter so that said protrusions are sealingly engaged with said conduits of said first lock adapter.

* * * * *